United States Patent [19]

Torenbeek

[11] Patent Number: 5,314,639
[45] Date of Patent: May 24, 1994

[54] AGGLOMERATION OF SOLID PEROXIDES

[75] Inventor: Reinder Torenbeek, Terwolde, Netherlands

[73] Assignee: Akzo N.V., Netherlands

[21] Appl. No.: 647,336

[22] Filed: Jan. 28, 1991

[30] Foreign Application Priority Data

Feb. 7, 1990 [EP] European Pat. Off. ......... 90200265.8

[51] Int. Cl.$^5$ .............................................. C01B 15/00
[52] U.S. Cl. ......................... 252/186.23; 252/186.21; 252/186.22; 252/186.26
[58] Field of Search ...................... 252/186.21, 186.23, 252/186.22, 186.26

[56] References Cited

U.S. PATENT DOCUMENTS

| 4,202,790 | 5/1980 | Steller | 252/186 |
| 4,401,835 | 8/1983 | Tarasov | 568/559 |
| 4,450,302 | 5/1984 | Willis | 502/150 |
| 4,515,929 | 5/1985 | Tang | 526/228 |
| 4,759,956 | 7/1988 | Amer et al. | 427/213 |
| 4,818,425 | 4/1989 | Meijer et al. | 252/94 X |
| 4,917,816 | 4/1990 | Self | 252/186.26 |
| 5,049,298 | 9/1991 | Ploumen et al. | 252/95 |
| 5,126,066 | 6/1992 | Torenbeek et al. | 252/95 |

FOREIGN PATENT DOCUMENTS

| 54029882 | 8/1976 | Japan . |
| 51096783 | 4/1980 | Japan . |
| 1081338 | 4/1965 | United Kingdom . |

OTHER PUBLICATIONS

Research Disclosure, 10 May 1980, No. 193002.

Primary Examiner—Richard D. Lovering
Assistant Examiner—Joseph D. Anthony
Attorney, Agent, or Firm—Ralph J. Mancini; Louis A. Morris

[57] ABSTRACT

The present application discloses a process for the production of agglomerates of peroxides that are solid at room temperature and which decompose rapidly when heated to their melting point. The process comprises agitating an aqueous suspension comprising a solid first peroxide which rapidly decomposes when heated to its melting point and a solid second peroxide which does not rapidly decompose when heated to its melting point and has a melting point which is substantially lower than the temperature at which said first peroxide rapidly decomposes, at a temperature sufficient to at least partially melt said second peroxide and below the decomposition temperature of said first peroxide to produce agglomerates comprised of said first and second peroxides; cooling with continued agitation the aqueous suspension having agglomerates to a temperature at which said second peroxide turns solid; and isolating the agglomerates. Also disclosed is a process such as that described above wherein a solvent immiscible with water is employed to aid the agglomeration process. The agglomerated peroxides are particularly useful in the polymerization of vinyl chloride monomers and the curing of unsaturated polyester resins.

8 Claims, No Drawings

AGGLOMERATION OF SOLID PEROXIDES

BACKGROUND OF THE INVENTION

The present invention relates generally to a process for the agglomeration of solid peroxides which rapidly decompose upon melting and to solid peroxide agglomerates made by this process.

Solid, organic peroxides are often obtained in the form of a lumpy, dusty powder having unacceptable flow characteristics which makes the handling and particularly the dosing of such peroxides extremely difficult. For example, when the peroxides contain too many fines they present difficult handling problems. In addition, the tendency of some peroxides to cake hampers their ability to dissolve in the reaction medium thereby significantly slowing commercial cross-linking processes. Accordingly, there is a need in the art to agglomerate solid organic peroxides to improve their flow properties, eliminate excess fines, provide a product with a narrow particle size distribution and to improve the dissolution time of such peroxides in reaction media.

A process for agglomerating solid peroxides is known from Japanese patent application JP 51-096783 published on Aug. 25, 1976. In this process, organic peroxide is melted and dispersed in a liquid medium in the presence of a high polymer surfactant and the dispersion liquid is then cooled to solidify the organic peroxide. While this process is satisfactory for some peroxides, it cannot be used for peroxides which rapidly decompose when heated to their melting points. Thus, this process is limited to peroxides which have melting points that are substantially lower than their decomposition temperatures.

Another process for agglomerating solid peroxides is known from *Research Disclosure* May 10, 1980, no. 193002, wherein it is taught to prepare peroxide granules by mixing a solid peroxide with a dispersing medium, heating the peroxide-containing medium to a temperature above the melting point of the peroxide and rapidly cooling the mixture. Again, this process is limited to peroxides which have melting points that are substantially below their decomposition temperatures since the process requires the melting of the peroxide.

U.S. Pat. No. 4,818,425 is representative of several publications which disclose processes for coating peroxyacids to be used in solid bleaching compositions. The coating is accomplished by agglomerating the peroxyacid in an aqueous suspension in the presence of a water-impermeable material which melts at a temperature substantially below the decomposition temperature of the peracid. In the agglomeration process, the aqueous suspension is agitated while being heated to a temperature above the melting point of the waterimpermeable material, and subsequently cooled to solidify the coated agglomerates of the peroxyacid. The purpose of this coating process is to prevent the occurrence of the phenomena termed pin point spotting when these peracids are employed as solid bleaching agents in textile laundering applications.

Finally, Japanese patent application JP 54-029882 published on Mar. 6, 1979 discloses a desensitized solid organic peroxide composition and a method for its preparation. In the method, a solid peroxide which is explosive to shock is wetted with water and added to additional water to produce an aqueous suspension. Up to 20 wt % of a second peroxide, which is nonexplosive, is dissolved in an organic solvent such as acetone and the solution of the second peroxide is mixed at room temperature with the suspension of the first peroxide and vigorously mixed to obtain a mixed solution containing a solid agglomerate which is subsequently separated and dried. While this process safely produces a desensitized agglomerate of the explosive peroxide, the resultant agglomerate exhibits an unacceptably wide particle size distribution and poor flow properties which make it difficult to handle.

The present invention has as its object to overcome the drawbacks of the prior art agglomeration processes listed above. Surprisingly, it has been found that the agglomeration process of the present invention provides an excellent method for providing solid organic peroxides which decompose upon melting in a form which is easier to handle and use than the presently available forms of these peroxides. More particularly, the present invention provides solid peroxides with a narrow particle size distribution, less fines, better flow properties, and, in some cases, better solubility in reaction media. All of these advantages are achieved while at the same time providing a safe agglomeration process and without introducing foreign materials into the product which significantly impair their efficacy for their intended use.

SUMMARY OF THE INVENTION

The present invention solves the problems of the prior art agglomeration methods by providing a process for the production of agglomerates of peroxides that are solid at room temperature and which decompose rapidly when heated to their melting point, said process comprising agitating an aqueous dispersion comprising a solid first peroxide which decomposes rapidly when heated to its melting point and a solid second peroxide which does not rapidly decompose when heated to its melting point and has a melting point which is substantially lower than the temperature at which said first peroxide rapidly decomposes, at a temperature sufficient to at least partially melt said second peroxide and below the decomposition temperature of said first peroxide; continuing said agitating to produce agglomerates comprised of both said first peroxide and second peroxide; cooling with continued agitation the aqueous suspension having agglomerates to a temperature at which said second peroxide turns solid; and isolating the agglomerates.

In addition, the present invention also relates to solid agglomerates containing two different peroxides which are produced by the process of the present invention.

DETAILED DESCRIPTION OF THE INVENTION

The underlying purpose of the present invention is to improve the properties of solid organic peroxides which rapidly decompose upon heating to their melting point. These peroxides present special problems in handling since they are often prone to violent decomposition. Further, these materials are generally obtained in the form of dusty, lumpy powders. It is highly desirable to transform such dusty, lumpy powders into a relatively uniform granulate which has improved flow properties and is not prone to caking during handling or use. Of course, all of these goals must be achieved without substantially altering the efficacy of these peroxides for their intended use in polymerization and cross-linking reactions. These objects of the present invention are achieved by the particular agglomeration process of the present invention.

Thus, the process of the present invention is applicable to the agglomeration of peroxides which are solid at room temperature and which undergo rapid decomposition when heated to their melting point. This class of peroxides, of which there are several, cannot be agglomerated by the classical melt agglomeration processes since the peroxide decomposes rather than melts.

Peroxides which decompose when heated to their melting temperature are well known in the art and many of them are described in *Organic Peroxides*, Swern et al., the disclosure of which is hereby incorporated by reference. A partial list of such peroxides which may be agglomerated by the process of the present invention includes benzoyl peroxides, cyclohexyl peroxy dicarbonates such as bis(4-tertiary butyl cyclohexyl) peroxydicarbonate; bis(p-chlorobenzoyl) peroxide, bis(2,4-dichlorobenzoyl) peroxide, dicyclohexyl peroxides such as 1-hydroxy-1'-hydroperoxy dicyclohexyl peroxide; 1,1-dihydroperoxycyclohexane, disuccinyl peroxide, peroxyacids such as 1,12-diperoxy dodecane dioic acid and nonylamidoperoxy succinic acid; 2,2-bis(4,4-ditertiary butyl peroxy cyclohexyl) propane, 1,4-bis(tertiary butyl peroxy isopropyl) benzene and the mono-tertiary butyl perester of maleic acid.

The amount of the first peroxide, which decomposes upon heating to its melting temperature, that should be present in the suspension is generally in the range of 2–40% by weight, preferably 5–25% by weight and more preferably 10–20% by weight, calculated on the weight of the total suspension. In general, it is useful to simply employ the first peroxide in the form of a wet filter cake which is obtained directly from the synthesis of these peroxides. Using the peroxide in this form eliminates the need for an intermediate drying step and effectively makes the agglomeration process of the present invention integratable into the peroxide manufacturing process itself.

The second peroxide, which acts as the binder or bridging material, must be a peroxide which undergoes little or no decomposition when melted. Further, a peroxide must be selected that has a melting point which is substantially below the decomposition temperature of the first peroxide so that at the melting point of the second peroxide, little or no decomposition of the first peroxide will occur. Thirdly, it is preferable to select a second peroxide which exhibits some useful activity in the field in which the first peroxide is to be employed. For example, if the first peroxide is to be employed for the polymerization of vinyl chloride monomers, a second peroxide should be selected that will also have some utility as an initiator for vinyl chloride polymerization. While second peroxides which are inert when used with the first peroxide, can be employed, it is more desirable that the second peroxide also participate in the end use to thereby provide a more effective product.

Solid second peroxides which are useful as bridging or binding materials in the agglomeration process of the present invention are generally known in the art. Typically these peroxides will have low melting points of 30°–80° C. and somewhat higher decomposition temperatures. Again, a listing of many peroxides meeting these criteria can be found in *Organic Peroxides*, Swern et al., the disclosure of which is hereby incorporated by reference. More particularly, useful second peroxides include, but are not limited to, dimyristyl peroxy dicarbonate, dicetyl peroxy dicarbonate, dilauroyl peroxide, didecanoyl peroxide, di-n-octanoyl peroxide, tertiary butyl peroxy stearylcarbonate, di-cumyl peroxide, and 1,3-bis(tertiary butyl peroxy isopropyl) benzene.

It will be clear that in the present process the second peroxide, in the molten state, acts as a binder liquid. It should be used in an amount of at least about 5% by weight, based on the weight of the first peroxide. The second peroxide may be added as a dry powder or as a wet filter cake, if desired. Generally, less than 100% by weight, based on the weight of the first peroxide should be employed although it is possible to employ larger amounts of the second peroxide in a particular embodiment of the present invention. For example, if a first peroxide with a particularly low decomposition temperature is to be agglomerated, large amounts of the second peroxide can be employed and heating applied to partially melt the second peroxide. Thus, since there is a large amount of the second peroxide, partial melting will provide enough binder material to agglomerate the remaining solid peroxide.

In some situations it may also be desirable to add to the peroxide suspension, as an additional component, a bridging liquid. In order for a bridging liquid to function it must preferentially wet the first peroxide and thereby displace water from the surface of the first peroxide and it must be immiscible with water. This embodiment is particularly usefully when, for example, the amount of the second peroxide which is present in the final agglomerate must be restricted. Thus, in place of additional second peroxide can be use this bridging liquid which enhances the agglomerative activity of the second peroxide. Then, after the agglomerates are formed, the bridging liquid can be removed by, for example, evaporative drying. In any event, generally at least 5% by weight of the agglomerate, must be the second peroxide in order that enough material is present to bind the agglomerates.

In order to enhance the agglomerative activity of the second peroxide, the solvent or bridging liquid should be employed in small amounts of up to 20% by weight, calculated on the weight of the first peroxide, and more preferably 2–10% of bridging liquid is employed.

Typical bridging liquids include nonpolar solvents or weakly polar solvents such as cyclohexane, hexane, boiling point spirits, toluene, chloroform and trichloroethylene. Since the binding action is proportional to the volume of the solvent, low density solvents are preferred.

The agglomeration process of the present invention is carried out in an aqueous suspension of said first and second peroxides. In the agglomeration process a suspension is first prepared and agitated. Then, the suspension, while still being agitated, is heated until it reaches the melting temperature of the second peroxide. At this point the suspension is generally maintained at this temperature for a period of a few minutes while melting of the second peroxide progresses and agglomeration of the two peroxides takes place. Once the agglomeration has proceeded to a sufficient degree to produce agglomerates of the desired size the suspension is immediately cooled to prevent further melting and agglomeration. The size of the agglomerates produced by the process can also be, to some extent, regulated by the degree of agitation applied during the agglomeration process.

The choice of the temperature at which the agglomeration is conducted is not only dependent upon the melting point of the second peroxide. The selection of temperature can also depend on other factors such as the desired viscosity of the binder which influences the duration of the agglomeration process as well as the size and strength of the agglomerates. In any case the temperature must be chosen to be below the temperature at which the first peroxide begins to rapidly decompose. A suitable temperature is generally one which is within about 5° C. of the melting point of the second peroxide.

It is not necessary in the process of the present invention to completely melt the second peroxide to accomplish agglomeration. In fact, under some circumstances it may be desirable to include a large excess of second peroxide in the suspension and then only partially melt the second peroxide to accomplish the agglomeration process. Thus, it is not critical that, during the agglomeration process, the suspension be maintained above the melting point of the second peroxide for any specific time period. Generally, the agglomeration process will be complete in less than thirty minutes from the time that the second peroxide begins to melt.

In a particularly favorable embodiment of the present invention the first peroxide is used in the form in which it is obtained directly from the synthesis process, either as a wet filter cake or in the mother liquor. A perfectly acceptable suspension of the first peroxide can be made simply by mixing the wet filter cake with water. This embodiment is advantageous because it eliminates the drying step which is normally carried out on the wet filter cake and it provides the ability to integrate the present agglomeration process into the overall synthesis process for these types of peroxides. It is also possible to eliminate the filtration step in some circumstances and simply carry out the agglomeration in the mother liquor used to make the first peroxide. While this embodiment may result in the incorporation of some salts from the mother liquor into the granules, the presence of such salts is no problem in some applications.

Once the agglomerate-containing suspension has cooled, preferably by rapid cooling, the agglomerates are then isolated from the suspension by, for example, filtration. The size of the agglomerates prepared may be varied by a suitable choice of the process variables. It is recommended that the process be carried out so as to produce agglomerates between 5 and 2000 μm in diameter and more preferably between 50 and 1000 μm in diameter. One of the most useful advantages of the present process is that it produces agglomerates having a relatively narrow particle size distribution such that the correct sized agglomerates are readily obtainable and the resultant products exhibit better flowability.

After the agglomerates have been isolated they may be dried in the usual manner. In some cases, where a bridging liquid has been employed, the drying process should also remove as much of the bridging liquid from the agglomerates as is reasonably possible.

The agglomerates of the present invention are particularly useful as initiators for polymerization reactions. More particularly, these agglomerates are useful in vinyl chloride polymerization or the polymerization of other, similar monomers. Further, the agglomerates of the present invention also find use in the curing of unsaturated polyesters.

In the field of polymerization of vinyl chloride monomers it has been found that the agglomerates of the present invention perform as well as or nearly as well as the same materials which have not been agglomerated. Thus, in view of the considerable advantages in the handling and dosing of these peroxides provided by the agglomeration process of the present invention, the agglomerates are considered better commercial products.

In the field of curing of unsaturated polyester resins, it has been found that the present agglomerates are at least as effective as the same materials which have not been agglomerated. Further, this application is often hampered by the tendency of the peroxide to cake and thereby dissolve in the unsaturated polyester resin at a much reduced rate. It has been found that the agglomerated peroxides produced by the process of the present invention do not suffer from this disadvantage and, in fact, dissolve much more rapidly in unsaturated polyester resin than the non-agglomerated peroxides.

The present invention will be further illustrated by the examples appended hereto.

EXAMPLE 1

Agglomeration of dibenzoyl peroxide with dilauroyl peroxide 50 grams of dibenzoyl peroxide were dispersed in 250 grams of water while mixing with an Ultra Turrax ® rotor-stator dissolver and a second, standard stirring apparatus and while heating this dispersion to 52° C., 18 grams of dilauroyl peroxide were added. After five minutes at 52° C. the mixture was rapidly cooled and the solid substance was isolated and dried. The particle size distribution, as determined by dry sieving, is shown in Table 1.

The free-flowing properties of the agglomerates were determined by letting 100 grams of the product flow out of funnels with orifices of 10, 20, 30 and 40 mm in diameter. This product passed the 10 mm orifice in 15 seconds and the 20 mm orifice in 2 seconds showing excellent free-flowing behavior.

EXAMPLE 2

Agglomeration of dibenzoyl peroxide with dilauroyl peroxide

Example 1 was repeated except that the material was stirred only by a standard stirring apparatus and the dispersion was maintained at 52° C. for a period of 7 minutes. The particle size distribution was determined by dry sieving and the results are shown in Table 1.

The free-flowing properties of these agglomerates were tested and it was found to exhibit excellent free-flowing behavior. It passed the 10 mm orifice in 16 seconds and the 20 mm orifice in 2 seconds.

Comparative Example A 50 grams of wet dibenzoyl peroxide, containing 20% water was added to 150 grams of water to obtain an aqueous suspension. 18 grams of dilauroyl peroxide was then dissolved in 18 ml of acetone to obtain a solution. The acetone solution and the aqueous suspension were then mixed vigorously in the manner described in Japanese patent publication JP-78-029882 to obtain a mixed solution containing a solid substance. The solid substance was separated and dried in a flow of air at room temperature. As a result, a capsule of dibenzoyl peroxide covered with dilauroyl peroxide was obtained. The particle size distribution was determined by dry sieving and is shown in Table 1.

The free-flowing properties of this material were determined in the same manner as is described in Example 1. It was found that the product could not flow through the 10 mm orifice and passed the 20 mm orifice in 8 seconds. Thus, the free-flowing behavior of this material was inferior to the materials of Examples 1 and 2 herein.

TABLE 1

| Particle size | Weight % | Active Oxygen (%) | BPO-content % (calculated from A.O.) |
|---|---|---|---|
| Material of Example 2 | | | |
| >3150 μm | <0.1 | — | — |
| 2000–3150 μm | 0.6 | 5.19 | 45 |
| 1000–2000 μm | 55.7 | 5.72 | 66 |
| 500–1000 μm | 42.8 | 5.84 | 70 |
| 250–500 μm | 0.8 | 5.95 | 74 |
| <250 μm | <0.1 | — | — |

| Particle size (dry sieved) | Weight % | Active Oxygen (%) | BPO-content % (calculated from A.O.) |
|---|---|---|---|
| Material of Comparative Example A | | | |
| >3150 μm | 0.3 | 5.20 | 45% |
| 2000–3150 μm | 1.3 | 5.10 | 42% |
| 1000–2000 μm | 18.8 | 5.61 | 61% |
| 500–1000 μm | 22.2 | 5.87 | 71% |
| 250–500 μm | 37.0 | 5.98 | 76% |
| 125–250 μm | 17.1 | 5.73 | 66% |
| 63–125 μm | 3.2 | 5.72 | 65% |
| <63 μm | <0.1 | | |
| Material of Example 1 | | | |
| >3150 μm | 0.0 | | |
| 2000–3150 μm | 0.0 | | |
| 1000–2000 μm | 3.3 | 5.79 | 68% |
| 500–1000 μm | 73.6 | 5.80 | 69% |
| 250–500 μm | 22.4 | 5.80 | 69% |
| 125–250 μm | 0.5 | 5.86 | 71% |
| 63–125 μm | 0.2 | | |
| <63 μm | <0.1 | | |

These results demonstrate that the agglomeration method of the present invention produces a more homogeneous, better flowing agglomerate with the lauroyl peroxide more evenly distributed than does the method of JP-78-029882. Both for safety and application reasons these are advantages since the prior art product may segregate upon handling or transport resulting in an inhomogeneous product.

EXAMPLE 3

Agglomeration of bis (4-tertiary butylcyclohexyl) peroxydicarbonate with dilauroyl peroxide In a 3 liter glass vessel, 492 grams of a wet cake of bis(4-tertiary butylcyclohexyl) peroxydicarbonate was dispersed in 1700 ml of water, stirred and heated to 50° C. 76 grams of dilauroylperoxide (purity 99.1%) was added and dispersed thoroughly. The mixture was cooled and the solid material was separated and dried. Thus, 99.9 wt. % was between 125 and 1000 microns in diameter. The active oxygen content was 3.87%. The free-flowing properties were demonstrated by the funnel-flow test wherein 100 grams passed through the 10 mm orifice in 19 seconds and through the 20 mm orifice in 3 seconds. The particle size distribution is shown in Table 2.

EXAMPLE 4

Agglomeration of bis(4-tertiary butylcycloheyxl) peroxydicarbonate with dicetyl peroxydicarbonate In the same manner as in Example 1, bis(4-tertiary butylcyclohexyl) peroxydicarbonate was agglomerated with dicetyl peroxydicarbonate at 56° C. Again, a free-flowing agglomerated material was obtained with 98.1 wt. % of the material being between 125 and 1000 microns in diameter. The active oxygen content wast. 3.43%. The particle size distribution is shown in Table 2.

EXAMPLE 5

Agglomeration of bis(4-tertiary butylcyclohexyl) peroxydicarbonate with dimyristyl peroxydicarbonate In the same manner as in Example 1, bis(4-tertiary butylcyclohexyl) peroxydicarbonate was agglomerated with dimyristyl peroxydicarbonate at 50° C. A free-flowing agglomerated material was obtained with an active oxygen content of 3.64% and 99.8 wt. % of the material having a diameter between 125 and 1000 m. The particle size distribution is shown in Table 2.

TABLE 2

| Mean Particle Size Distribution of Initiator Agglomerates | | | |
|---|---|---|---|
| Sieve analysis | Example 3 | Example 4 | Example 5 |
| <32 micron (%) | 0 | 0 | 0 |
| on 32 micron (%) | 0 | 0.1 | 0.1 |
| 63 micron (%) | 0.1 | 1.3 | 0.2 |
| 125 micron (%) | 2.2 | 5.8 | 1.0 |
| 250 micron (%) | 86.0 | 43.0 | 9.3 |
| 500 micron (%) | 11.7 | 49.3 | 88.3 |
| 1000 micron (%) | 0.1 | 0.4 | 1.2 |
| Mean particle size (micron) | 385 | 500 | 635 |
| Spread (%) | 44.2 | 69.0 | 39.3 |
| A.O. Content (%) | 3.87 | 3.43 | 3.63 |

EXAMPLES 6–8

Polymerization of Vinyl Chloride Monomers With the Agglomerates of the Present Invention The 1 liter Büchi stainless steel autoclave with stirrier and baffle is filled with the aqueous protective colloid solution in which the phosphate buffer is solved. The initiator is added. The reactor is evacuated and flushed with nitrogen four times while stirring, followed by addition of the vinyl chloride monomer (VCM) at ambient temperature. The polymerization is started by heating to a reaction temperature of 57° C. in 60 minutes. After 7 hours, the reactor is cooled and excess VCM vented. The PVC is filtered, washed, dried overnight at 50° C., weighed and analyzed.

| Analysis | |
|---|---|
| Conversion: | by weighing |
| Bulk density: | Erichsen DIN cup 243/11.8 |
| Dry flow: | " |
| Mean particle size, PVC: | Coulter Counter (multisizer) |
| Mean particle size, initiator: | ASTM D 1971 - 61 T |
| Recipe for Reactant Mixture | |
| 260 g VCM | |
| 520 H$_2$O | |
| 0.1 g Na$_2$HPO$_4$ | |
| 0.1 g NaH$_2$PO$_4$ | |
| 0.11% Gohsenol KP-08 (based on VCM) | |

The initiators of Examples 3–5 were employed in Examples 6–8, respectively. The amounts of initiator used as well as the properties of the resultant PVC are shown in Table 3.

TABLE 3

VCM Polymerization at 57° C. Initiated by Different Initiators

| Initiator | Conv. (%) | Bulk density (g/cm3) | Dry flow (g/sec) | Press. drop (bar) | Particle size (micron) | (spread in %) |
|---|---|---|---|---|---|---|
| 0.06% bis(4-tertiary butylcyclohexyl peroxydicarbonate (Standard) | 88.3 | 0.443 | 3.7 | 2.87 | 183 | 43 |
| 0.0649% From Example 4 | 89.2 | 0.426 | 3.6 | 3.21 | 192 | 43 |
| 0.0636% From Example 5 | 88.8 | 0.432 | 3.8 | 3.04 | 193 | 39 |
| 0.06% From Example 3 | 84.0 | 0.438 | 3.7 | 2.00 | 190 | 41 |
| 0.08% From Example 3 | 89.6 | 0.434 | 3.7 | 3.53 | 191 | 44 |

The results of Table 3 demonstrate that the agglomerates prepared in accordance with the present invention gave substantially the same results when used in the initiation of vinyl chloride polymerization as the substantially pure bis(4-tertiary butylcyclohexyl)peroxydicarbonate apart from a small coarsening effect on the particle size of the PVC. Amounts of the materials were adjusted to provide identical active oxygen contents in each case. Only agglomerates with lauroyl peroxide gave slightly inferior results which were expected from the lower initiation activity of lauroyl peroxide. This problem was simply solved by slightly increasing the amount of agglomerated peroxide employed as the initiator as is demonstrated by the last example in Table 3.

EXAMPLE 9

The percentage of fine dust was determined with a "Heubach" dust determination apparatus. In commercial bis(4-tertiary butylcyclohexyl)peroxydicarbonate a dust content of 3.1% was found whereas in the agglomerates of Examples 3-5 dust contents of about 0.2% were found. This demonstrates that the agglomeration process of the present invention significantly reduces the dust content of the solid peroxide materials.

EXAMPLES 10-11

These examples demonstrate the advantage of using the agglomerates of the present invention as compared with using pure bis(4-tertiary butylcyclohexyl)peroxydicarbonate in the cure of unsaturated polyester resins. Pure bis(4-tertiary butylcyclohexyl)peroxydicarbonate is normally used in the cure of unsaturated polyester resins to obtain a fast cure at moderately elevated temperatures. This application is hampered, however, by the slow dissolution of commercial grade bis(4-tertiary butylcyclohexyl) peroxydicarbonate in unsaturated polyester, mainly due to the tendency of the material to "cake". The agglomerates of the present invention do not "cake" and, in fact, exhibit a surprisingly faster dissolution rate in unsaturated polyester. This was demonstrated by the following procedure.

In a 250 ml glass beaker, 100 grams of unsaturated polyester (Ludopal p6, ex. BASF) was stirred with a toothed disc dissolver (disc diameter 35 mm) at 400 rpm. 1 gram of the peroxide was admixed. The dissolution times of the peroxides are shown in Table 4.

TABLE 4

| Sample | Dissolution time |
|---|---|
| Bis(4-tertiarybutylcyclohexyl) Peroxycarbonate (Standard) | 19.0 minutes |
| Agglomerate of Example 4 | 3.1 minutes |
| Agglomerate of Example 3 | 3.4 minutes |

This clearly demonstrates that the agglomerates of the present invention dissolve about 6 times faster than commercial grade bis(4-tertiary butylcyclohexyl)peroxydicarbonate.

The foregoing examples were presented for the purpose of illustration and description only and are not to be construed as limiting the scope of the invention in any way. The scope of the invention is to be determined from the claims appended hereto.

I claim:

1. A process for the production of agglomerates of organic peroxides that are solid at room temperature and which decompose rapidly when heated to their melting point, said process comprising agitating an aqueous suspension comprising a solid first peroxide which decomposes rapidly when heated to its melting point and a solid second peroxide which does not rapidly decompose when heated to its melting point and has a melting point which is substantially lower than the temperature at which said first peroxide rapidly decomposes, at a temperature sufficient to at least partially melt said second peroxide and below the decomposition temperature of said first peroxide, wherein said second peroxide is present in the aqueous suspension in an amount of from 5-100% by weight, based on said first peroxide continuing said agitating to produce agglomerates comprised of both said first peroxide and second peroxide; cooling with continued agitation the aqueous suspension having agglomerates to a temperature at which said second peroxide turns solid; and isolating the agglomerates.

2. A process of claim 1 wherein said second peroxide is present in the aqueous suspension in an amount of from 10-70% by weight, based on said first peroxide.

3. A process of claim 1 wherein said second peroxide is selected from the group consisting of dimyristyl peroxy dicarbonate, dicetyl peroxy dicarbonate, dilauroyl peroxide, didecanoyl peroxide, di-n-octanoyl peroxide, tertiary butyl peroxy stearyl carbonate, dicumyl peroxide and 1,3-bis(tertiary butyl peroxy isopropyl) benzene.

4. A process of claim 1 wherein said first peroxide is selected from the group consisting of benzoyl peroxides, cyclohexyl peroxy dicarbonates, bis(p-chlorobenzoyl)peroxide, bis(2,4-dichlorobenzoyl) peroxide, dicyclohexyl peroxides, 1,1-dihydroperoxycyclohexane, disuccinyl peroxide, peroxyacids, 2,2-bis(4,4-ditertiary butyl peroxy cyclohexyl) propane, 1,4-bis(tertiary butyl peroxy isopropyl) benzene and the monotertiary butyl perester of maleic acid.

5. A process of claim 4 wherein said first peroxide is selected from the group consisting of 1,12 diperoxy dodecanedioic acid, dibenzoyl peroxide and bis(4-tertiary butyl cyclohexyl) peroxy dicarbonate.

6. A process of claim 1, wherein said aqueous suspension further comprises a solvent which is immiscible with water and preferentially wets said first peroxide, said solvent present in a sufficient amount to enhance the agglomerative activity of said second peroxide.

7. A process of claim 6 further comprising removing substantially all of said solvent from said agglomerates by drying.

8. A process of claim 6 wherein said solvent is selected from the group consisting of nonpolar solvents.

* * * * *